United States Patent
Gerber et al.

(10) Patent No.: US 9,012,215 B2
(45) Date of Patent: Apr. 21, 2015

(54) METHODS FOR IDENTIFYING LEUKEMIA STEM CELLS AND DISTINGUISHING THEM FROM NORMAL HEMATOPIETIC STEM CELLS IN PATIENTS WITH ACUTE MYELOID LEUKEMIA: USES IN DIAGNOSIS, TREATMENT, AND RESEARCH

(71) Applicants: Jonathan Michael Gerber, Baltimore, MD (US); Richard John Jones, Baltimore, MD (US)

(72) Inventors: Jonathan Michael Gerber, Baltimore, MD (US); Richard John Jones, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/625,369

(22) Filed: Sep. 24, 2012

(65) Prior Publication Data
US 2013/0079424 A1  Mar. 28, 2013

Related U.S. Application Data

(60) Provisional application No. 61/537,632, filed on Sep. 22, 2011.

(51) Int. Cl.
*C12N 5/095* (2010.01)
*C12N 5/09* (2010.01)
*G01N 33/574* (2006.01)
*C12Q 1/32* (2006.01)

(52) U.S. Cl.
CPC ............ *C12Q 1/32* (2013.01); *G01N 33/57426* (2013.01); *G01N 2800/54* (2013.01)

(58) Field of Classification Search
CPC ........... G01N 33/57426; C12N 5/0694; C12N 5/0695
See application file for complete search history.

(56) References Cited

U.S. PATENT DOCUMENTS

2008/0118432 A1* 5/2008 Bergstein et al. ............ 424/1.49

OTHER PUBLICATIONS

Terwijn ("Acute Detection of Residual Leukemic Stem Cells in Remission Bone Marrow Predicts Relapse in Acute Myeloid Leukemia Patients", American Society of Hematology, 53rd ASH Annual Meeting and Exposition, Dec. 2010, Abstract provided).*
Pearce ("Characterization of Cells with a High Aldehyde Dehydrogenase Activity from Cord Blood and Acute Myeloid Leukemia Samples" Stem Cells, 2005, 23, 752-760.*
Gerber ("A clinically relevant population of Leukemic CD34+CD38—cells in acute myeloid Leukemia" Blood, 2012, vol. 119 No. 15, 3571-3577).*
Cheung ("Aldehyde dehydrogenase activity in leukemic blasts defines a subgroup of acute myeloid leukemia with adverse prognosis and superior NOD/SCID engrafting potential" Leukemia (2007), 21, 1423-1430).*
Ran ("Aldehyde dehydrogenase activity among primary leukemia cells is associate with stem cell features and correlates with adverse clinical outcomes" Experimental Hematology, 2009, 37, 1423-1434.*

* cited by examiner

*Primary Examiner* — Blaine Lankford
*Assistant Examiner* — Charles Zoltan Constantine
(74) *Attorney, Agent, or Firm* — Johns Hopkins Technology Transfer

(57) ABSTRACT

Using the methods of the present invention, intermediate (int) levels of aldehyde dehydrogenase (ALDH) activity reliably distinguished leukemic $CD34^+CD38^-$ cells capable of engrafting immunodeficient mice, from residual normal hematopoietic stem cells that exhibited relatively higher ALDH activity. Minimal residual disease (MRD) detected during complete remission was enriched for the $CD34^+CD38^-ALDH^{int}$ leukemic cells, and the presence of these cells after therapy highly correlated with subsequent clinical relapse. The methods of the present invention can distinguish normal from leukemic $CD34^+CD38^-$ cells, and identifies those AML cells associated with relapse. Methods of prediction of relapse of AML patients and methods of treatment are also provided.

13 Claims, 4 Drawing Sheets

FIGURE 6: Detection of the $CD34^+CD38^-ALDH^{int}$ population in available follow-up samples of AML patients who achieved morphologic complete remission.

| Patient # | Post-Induction/ Pre-Consolidation | During Consolidation | Time Post-Consolidation | | | | | | Outcome |
|---|---|---|---|---|---|---|---|---|---|
| | | | 0-6 months | 6-12 months | 12-18 months | 18-24 months | 24-36 months | 36-48 months | |
| 1 | Absent | | Present | | | | | | Relapsed 34 days after detection |
| 2 | | | Absent | Absent | Absent | Absent | | | CRi 688 days since diagnosis |
| 3 | Absent | | Absent | | | | | | CR 264 days since diagnosis |
| 7 | | | Absent | Present | | | | | Relapsed 32 days after detection |
| 10 | Absent | Absent | Absent | | | | | | CR 323 days since diagnosis |
| 11 | | Absent | Absent | | | | | | CR 508 days since diagnosis |
| 12 | Present | | | | | | | | Relapsed 25 days after detection |
| 13 | Absent | | Absent | | | | | | CR 185 days since diagnosis |
| 14 | | | | Present | | | | | Relapsed 62 days after detection |
| 15 | Present | | | | | | | | Relapsed 33 days after detection |
| 16 | Present | | | | | | | | CR 435 days after allogeneic HSCT |
| 17 | | | Absent | Absent | Absent | Absent | Absent | | CR 810 days since diagnosis |
| 18 | Absent | | Present | | | | | | Relapsed 81 days after detection |
| 19 | | | | | | | Absent | Absent | CR 1117 days since diagnosis |
| 20 | | | Absent | Absent | | | | | CR 379 days since diagnosis |
| 21 | | | | | | | Absent | Absent | CRi 1208 days since diagnosis |

METHODS FOR IDENTIFYING LEUKEMIA STEM CELLS AND DISTINGUISHING THEM FROM NORMAL HEMATOPIETIC STEM CELLS IN PATIENTS WITH ACUTE MYELOID LEUKEMIA: USES IN DIAGNOSIS, TREATMENT, AND RESEARCH

REFERENCE TO RELATED APPLICATIONS

This application claims the benefit of U.S. Provisional Patent Application No. 61/537,632, filed on Sep. 22, 2011, which is hereby incorporated by reference for all purposes as if fully set forth herein.

STATEMENT OF GOVERNMENTAL INTEREST

This invention was made with U.S. government support under grant nos. P01 CA15396, P01 CA070970, U01 CA70095, and 5T32 HL007525. The U.S. government has certain rights in the invention.

BACKGROUND OF THE INVENTION

Although most patients with acute myeloid leukemia (AML) achieve complete remission (CR) following standard induction chemotherapy, the majority subsequently relapses and succumbs to the disease. A leukemia stem cell (LSC) paradigm may explain this failure of CR to reliably translate into cure. Leukemia appears to retain some semblance of the normal hematopoietic hierarchical structure: i.e., rare LSCs with self-renewal capacity give rise to partially differentiated progeny that comprise the bulk of the leukemia but possess only limited proliferative potential. It is theorized that existing therapies, although highly active against the leukemic bulk, often spare the hardier LSCs responsible for relapse.

Since the 1994 report by Dick and colleagues that only the rare AML cells characterized by a $CD34^+CD38^-$ phenotype were capable of generating leukemia in immunodeficient mice, these putative LSCs have been the focus of considerable research. However, even in leukemia where the cancer stem cell (CSC) concept is perhaps best established, there is a paucity of data that LSCs are in fact responsible for disease resistance or relapse. Although it is generally accepted that $CD34^+CD38^-$ cells are enriched for LSCs, this population is heterogeneous and includes both normal and leukemic cells. Moreover, recent data have challenged the $CD34^+CD38^-$ phenotype of LSCs in AML, leading many investigators to advocate for a functional definition LSCs: those leukemic cells capable of engrafting immunodeficient mice. However, this current gold standard for the identification of LSCs has proven to be somewhat elusive. A significant fraction of AML samples will not engraft mice, and the assay is cumbersome and often non-quantitative. Additionally, the clinical implications of this assay are unclear.

If $CD34^+CD38^-$ leukemic cells are indeed clinically relevant, then minimal residual disease (MRD)—any microscopic disease remaining during CR—should be relatively enriched for these cells; and their persistence after therapy should correlate with recurrence.

Therefore, there still exists a need for identifying LSC in patients with AML so that the patients can be identified as having a high or low risk for relapse and appropriate treatment can be delivered.

SUMMARY OF THE INVENTION

In accordance with an embodiment, the present invention provides a method for identifying the presence of leukemia stem cells (LSC) in a sample from a subject suffering from AML comprising: a) obtaining a biological sample from a subject; b) isolating $CD34^+CD38^-$ mononuclear cells or population of cells from the sample; c) measuring the ALDH activity of the cells or population of cells of b); and d) identifying the cells from c) that have a intermediate level of ALDH activity ($CD34^+CD38^-ALDH^{int}$) as being LSC.

In accordance with another embodiment, the present invention provides a method for prediction of an increased risk of relapse after treatment in a subject suffering from AML comprising: a) treating the subject suffering from AML with appropriate therapy; b) obtaining a post-therapy biological sample from a subject; c) isolating $CD34^+CD38^-$ mononuclear cells or population of cells from the sample; d) measuring the ALDH activity of the cells or population of cells of c); e) identifying the cells from c) that have a intermediate level of ALDH activity ($CD34^+CD38^-ALDH^{int}$) as being LSC; and f) determining that the subject has an increased risk for relapse of AML, and/or require further treatment, when the presence of LSC are detected.

In accordance with a further embodiment, the present invention provides a method for treatment of a subject suffering from AML comprising: a) obtaining a pre- and/or post-therapy biological sample from a subject; b) isolating $CD34^+CD38^-$ mononuclear cells or population of cells from the sample; c) measuring the ALDH activity of the cells or population of cells of b); d) identifying the cells from c) that have a intermediate level of ALDH activity ($CD34^+CD38^-ALDH^{int}$) as being LSC; e) treating the subject suffering from AML with appropriate therapy; f) repeating steps a) to e); and g) determining that the subject has completed treatment for AML when the presence of LSC are not detected.

BRIEF DESCRIPTION OF THE DRAWINGS

FIG. 6 depicts the detection of the CD34+CD38−ALDH$^{int}$ population in available serial follow-up samples and correlation with the clinical outcomes of AML patients who achieved morphologic complete remission (CR) after induction therapy. Persistence of the CD34+CD38−ALDH$^{int}$ population strongly correlated with relapse; 6 of 7 patients with this population present have since relapsed (25-81 days after detection), with the lone exception a patient who proceeded directly to allogeneic hematopoietic stem cell transplantation. In contrast, the CD34+CD38−ALDH$^{int}$ population remains undetectable (absent) in the other 9 patients, all of whom are still in CR, including 3 patients in CR>2 years (p<0.01 by Fisher's exact test).

DETAILED DESCRIPTION OF THE INVENTION

Figure 1:
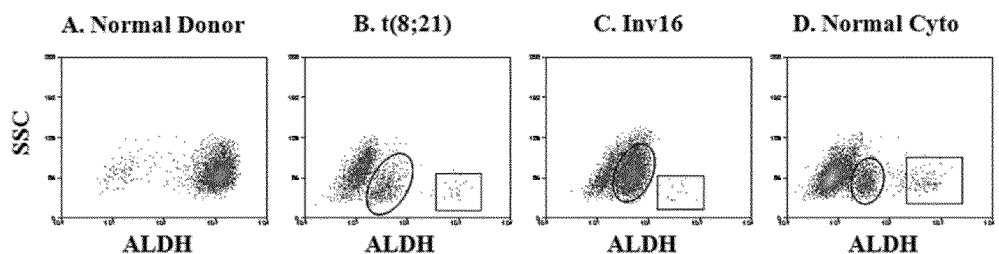
FIG. 1 depicts staining patterns of a normal donor and diagnostic AML samples. Representative flow cytometric staining patterns of aldehyde dehydrogenase (ALDH) activity by side scatter (SSC) are displayed for $CD34^+CD38^-$ cells isolated from: (A) a normal donor, (B) a patient (#9) with t(8; 21) AML, (C) a patient (#1) with Inv16 AML, and (D) a patient (#17) with normal cytogenetic (cyto) AML. The AML samples, but not the normal marrows, contained a discrete $CD34^+CD38-ALDH^{int}$ population (circled). In the patients with core-binding factor (CBF) AML, this $CD34^+CD38^-ALDH^{int}$ population was essentially completely leukemic by FISH. The $CD34^+CD38^-ALDH^{low}$ population from the CBF AMLs was also almost entirely leukemic by FISH. In contrast, the small $CD34^+CD38^-ALDH^{high}$ populations (boxed) from CBF AML patients lacked the leukemia-specific FISH marker. The percentage of $CD34^+CD38^-$ cells comprised by the $CD34^+CD38^-ALDH^{int}$ and $CD34^+CD38^-ALDH^{high}$ populations are listed on each dot plot.

Relapse of AML is thought to reflect the failure of current therapies to adequately target LSCs—the rare, resistant cells presumed responsible for maintenance of the leukemia, which are typically enriched in the CD34+CD38− cell population. Despite the considerable research on LSCs over the past two decades, the clinical significance of these cells remains uncertain. However, LSCs would be expected to be enriched in MRD and predictive of relapse.

In accordance with the inventive methods, CD34+ subpopulations from AML patients were analyzed by flow cytometry throughout treatment. Sorted cell populations were analyzed by fluorescence in situ hybridization for leukemia-specific cytogenetic abnormalities (when present) and by transplantation into immunodeficient mice to determine self-renewal capacity. Intermediate (int) levels of aldehyde dehydrogenase (ALDH) activity reliably distinguished leukemic CD34+CD38− cells capable of engrafting immunodeficient mice from residual normal hematopoietic stem cells that exhibited relatively higher ALDH activity. MRD detected during complete remission was enriched for the CD34+CD38−ALDH$^{int}$ leukemic cells, and the presence of these cells after therapy highly correlated with subsequent clinical relapse.

As such, the embodiments of the methods of the present invention show that ALDH activity distinguishes normal from leukemic CD34+CD38− cells which have both low (ALDH$^{low}$) and high (ALDH$^{high}$) levels of ALDH activity, and identifies those AML cells associated with relapse.

In accordance with an embodiment, the present invention provides a method for identifying the presence of leukemic stem cells (LSC) in a sample from a subject suffering from AML comprising: a) obtaining a biological sample from a subject; b) isolating CD34+CD38− mononuclear cells or population of cells from the sample; c) measuring the ALDH activity of the cells or population of cells of b); and d) identifying the cells from c) that have a intermediate level of ALDH activity (CD34+CD38− ALDH$^{int}$) as being LSC.

In accordance with one or more embodiments of the present invention, it will be understood that the term "biological sample" or "biological fluid" includes, but is not limited to, any quantity of a substance from a living or formerly living patient or mammal which can contain CD34+CD38− cells. Such substances include, but are not limited to, blood, serum, plasma, urine, cells, organs, tissues, bone, bone marrow, lymph, lymph nodes, cerebrospinal fluid and tumors.

As used herein, the term ALDH$^{int}$ means CD3$^{4+}$CD3$^{8−}$ cells having an intermediate level of ALDH activity relative to the ALDH levels of normal controls, which can have low or high ALDH activity.

As used herein, the term "isolating" with regard to the CD34+ cells includes separating the cells from the biological sample can be performed using any well known means in the art. In an embodiment, the separation is performed using a ficoll gradient and centrifugation, followed by enrichment using a CD34+ antibody column or similar means.

The CD34+ cells can be labeled using any known labeled conjugate to anti-CD34 and anti-CD38 antibodies, where the conjugates have detectable labels that can be differentiated from each other. In an embodiment, the CD34+ cells labeled with monoclonal phycoerythrin-conjugated anti-CD34 and allophycocyanin (APC)-conjugated anti-CD38 which fluoresce at different wavelengths.

By "detectable label(s) or moieties" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

To asses ALDH activity of the CD34$^+$ cells, the cells are contacted with a fluorescent ALDH substrate which is taken up by the cells, where ALDH cleaves the substrate and allows the fluorescent compound to be retained in the intact living cell where it can be detected using a fluorimeter or fluorescence cell sorter (FACS) device. In an embodiment, the CD34$^+$ cells are labeled using Aldefluor which comprises a biodipy fluorescent ligand attached to aminoacetate. It will be understood by those of skill that any similar labeled substrate can be used with the methods of the present invention.

Those of ordinary skill in the art will understand that the order in which the CD34$^+$ cells are labeled for ALDH activity and then labeled to detect CD34$^+$ and CD38$^-$ cells is not significant. The cells can be labeled in any order as long as all of the labeling is completed before detection and analysis.

It will be understood that the methods of the present invention which determine the ALDH activity of the CD34$^+$CD38$^-$ cells are useful in preclinical research activities as well as in clinical research in various diseases or disorders, including, for example, AML. The methods of the present invention can identify those subjects who require further treatment (i.e., those in whom the ALDH$^{int}$ cells persist); this may also serve as an early surrogate for leukemia-free survival.

In accordance with an embodiment, the present invention provides methods that allow AML LSCs to be viably isolated and distinguished from normal HSCs. As described herein, the inventive methods allow for identification of putative therapeutic targets and can be used to simultaneously assess a therapy's toxicity against normal hematopoietic stem cells while assessing its effectiveness against LSCs.

In accordance with another embodiment, the present invention provides a method for prediction of an increased risk of relapse after treatment in a subject suffering from AML comprising: a) treating the subject suffering from AML with appropriate therapy; b) obtaining a post-therapy biological sample from a subject; c) isolating CD34$^+$CD38$^-$ mononuclear cells or population of cells from the sample; d) measuring the ALDH activity of the cells or population of cells of c); e) identifying the cells from d) that have a intermediate level of ALDH activity (CD34$^+$CD38$^-$ALDH$^{int}$) as being LSC; and f) determining that the subject has an increased risk for relapse of AML, and/or requires further treatment, when the presence of LSC are detected.

The inventive methods can be used to assist in the clinical assessment of AML patients who have undergone treatment, including chemotherapeutic treatment or bone marrow ablation and transplantation, to determine if there is any identifiable population of LSC, based on detection and/or presence of CD34$^+$CD38$^-$ALDH$^{int}$ cells in one or more biological samples from the patient. These methods can be used to periodically reassess the AML patients to monitor the course of treatment and treatment outcome over time.

In accordance with a further embodiment, the present invention provides a method for treatment of a subject suffering from AML comprising: a) obtaining a pre- and/or post-therapy biological sample from a subject; b) isolating CD34$^+$CD38$^-$ mononuclear cells or population of cells from the sample; c) measuring the ALDH activity of the cells or population of cells of b); d) identifying the cells from c) that have a intermediate level of ALDH activity (CD34$^+$CD38$^-$ALDH$^{int}$) as being LSC; e) treating the subject suffering from AML with appropriate therapy; f) repeating steps a) to e); and g) determining that the subject has completed treatment for AML when the presence of LSC are not detected.

The inventive methods can also be used to help choose the type of treatment an AML patient may receive and can be also used to clinically assess whether the treatment being used is effective.

The phrase "controls or control materials" or "normal" refers to any standard or reference tissue or material that has not been identified as having cancer, such as AML.

The term "biologically active" as used herein means an enzyme or protein having structural, regulatory, or biochemical functions of a naturally occurring molecule.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, screening, or other patient management, including treatment or prevention of cancer in a mammal.

In accordance with an embodiment, the present invention provides a method for identifying the presence of leukemia stem cells (LSC) in a sample from a subject suffering from Acute Myeloid Leukemia (AML) comprising: a) obtaining a biological sample from the bone marrow of a subject; b) isolating CD34$^+$ mononuclear cells from the sample; c) contacting the CD34$^+$ mononuclear cells with an ALDH sensitive dye to identify ALDH activity in the cells, and with labeled anti-CD34 and labeled anti-CD38 antibodies; d) analyzing the cells from c) using fluorescence detection; and e) identifying the LSC, those cells and/or population of cells from d) which are determined to have bound anti-CD34 antibodies and not bound anti-CD38 antibodies and also have a intermediate level of ALDH activity (CD34$^+$CD38$^-$ALDH$^{int}$) when compared to CD34$^+$CD38$^-$ cells and/or population of cells having low ALDH activity (ALDH$^{low}$) and/or having high ALDH activity (ALDH$^{high}$) in the subject.

EXAMPLES

Human samples. Bone marrow was procured from a total of 27 AML patients (Table 1). All research samples represented excess bone marrow collected at diagnosis or during routine follow-up. Excess bone marrow from the harvests of ten normal donors for allogeneic bone marrow transplantation was also studied. Specimens were collected between April 2008 and April 2011, by the Johns Hopkins Kimmel Cancer Center Specimen Accessioning Core. Appropriate informed consent was obtained from all patients and normal donors prior to specimen collection, in accordance with the Declaration of Helsinki and under a research protocol approved by the Johns Hopkins Institutional Review Board. Samples were obtained from 20 of the AML patients at initial diagnosis. An additional seven patients who had already begun treatment at the time of first sample procurement were also studied. Initially, in an attempt to limit heterogeneity and ensure the presence of a detectable, leukemia-specific abnormality, specimens were restricted to patients with core-binding factor (CBF) AML. Later, the sample pool was expanded to all cases of AML except acute promyelocytic leukemia, which was excluded due to its uniquely favorable prognosis and distinct treatment approach. AML induction regimens consisted of cytarabine, daunorubicin, and etoposide or a clinical trial of flavopiridol, cytarabine, and mitoxantrone (FLAM). Consolidation therapy consisted of cytarabine plus daunorubicin, high-dose cytarabine, or FLAM. Patients who achieved morphologic CR with induction chemotherapy were followed until relapse or their last available bone marrow specimen. All analyzed research specimens are reported.

Isolation of cells. CD34$^+$ cell subsets were identified and isolated as we previously described. Briefly, mononuclear cells were isolated by density gradient centrifugation (Ficoll-Paque, GE Healthcare Life Sciences, Piscataway, N.J.); and CD34$^+$ cells were then selected via magnetic bead and column (Miltenyi Biotec, Auburn, Calif.). Samples were then viably cryopreserved in 90% fetal bovine serum and 10% DMSO (Sigma-Aldrich, St. Louis, Mo.) and stored until further use. Following thawing and washing, cells were then stained with Aldefluor (Aldagen, Durham, N.C.) to assess ALDH activity. Next, cells were labeled with monoclonal phycoerythrin-conjugated anti-CD34 and allophycocyanin (APC)-conjugated anti-CD38 (BD Biosciences, San Jose, Calif.), then analyzed and sorted using a MoFlo cell sorter (Beckman Coulter, Brea, Calif.) at the Johns Hopkins Bloomberg School of Public Health Flow Cytometry Core.

Fluorescence in situ hybridization (FISH). For those patients with cytogenetic abnormalities detectable by FISH,

TABLE 1

Patient clinical and demographic characteristics.

| Patient | Cytogenetics | AML type | Age | Sex | Race | Outcome | Other Comments |
|---|---|---|---|---|---|---|---|
| 1 | Complex, including Inv16 | De novo | 44 | M | W | Relapsed | |
| 2 | Inv16 & +8 | Treatment-related | 64 | F | W | CRp | |
| 3 | Inv16 & +22 | De novo | 50 | F | W | CR | |
| 4 | Inv16 & +8 | De novo | 23 | F | W | CR | |
| 5 | Inv16 | De novo | 58 | F | AA | Relapsed | |
| 6 | Inv16 & FLT3 D835 (constitutional 47, XXY) | De novo | 40 | M | W | Died | died during induction |
| 7* | t(8; 21) | Treatment-related | 51 | F | W | Relapsed | |
| 8 | t(8; 21) & FLT3 D835 | De nova | 54 | M | W | Relapsed | did not receive consolidation |
| 9 | t(8; 21) | De novo | 24 | M | H | Relapsed | |
| 10 | t(8; 21) | De novo | 27 | M | O | CR | |
| 11 | t(8; 21) & del 12p | De novo | 49 | M | W | CR | |
| 12 | +21 | Treatment-related MDS/AML | 64 | M | W | Died | died of infection while relapsing |
| 13 | +11 | CMML/AML | 54 | M | W | CR | |
| 14* | Normal | De novo | 44 | F | W | Relapsed | CR2 after allogeneic transplantation |
| 15* | Complex, including +21 | Treatment-related MDS/AML | 64 | F | W | Relapsed | likely constitutional +X |
| 16* | Complex, including del 7q | De novo | 34 | F | O | CR | s/p allogeneic transplantation |
| 17 | Normal | De novo | 54 | M | W | CRp | |
| 18 | Normal with FLT3 D835 | De novo | 69 | M | W | Relapsed | 3/20 metaphases with +13 |
| 19* | t(8; 21) & del Y | De novo | 49 | M | W | CR | |
| 20* | t(8; 21) | De novo | 55 | M | AA | CR | |
| 21* | Normal | De novo | 48 | M | W | CRi | |
| 22 | Inv16 & FLT3 D835 | De novo | 38 | M | W | CR | |
| 23 | Normal | De novo | 61 | M | AA | Primary Refractory | |
| 24 | Normal with FLT3 ITD | De novo | 21 | F | W | Primary refractory | |
| 25 | Complex, including del 5 & del 7 | De novo | 57 | M | W | Primary refractory | |
| 26 | t(9; 11) & +8 | De novo | 58 | F | AA | Relapsed | CD34- Leukemia |
| 27 | +8, FLT3 ITD, & NPM1 | De novo | 58 | F | AA | CR | CD34- leukemia |

250-1000 cell aliquots were sorted directly onto slides and then fixed with 3:1 methanol-glacial acetic acid (Sigma-Aldrich, St. Louis, Mo.). All research and clinical FISH was performed and analyzed by the Johns Hopkins Kimmel Cancer Center Cytogenetics Core, using probes specific for the patient's known cytogenetic abnormality, per manufacturer's guidelines (Abbot Molecular, Des Plaines, Ill.).

NOD/SCID-IL2Rγ$^{null}$ (NSG) mouse engraftment. NSG mice received 300cGy irradiation and then were injected via tail vein with $10^3$-$10^5$ cells of the CD34$^+$ cell subpopulations obtained from a normal donor or AML patient, as we previously described (*Am. J. Hematol.*, 2011; 86:31-37). Mice were sacrificed 3-4 months later, and their bone marrow was harvested. The harvested mouse bone marrow was treated with RBC lysis buffer (Sigma-Aldrich) and labeled with an APC-conjugated monoclonal antibody against human CD45 (BD Biosciences). The human CD45$^+$ population was sorted directly onto slides for analysis by FISH. All mouse research was performed under a protocol approved by the Johns Hopkins Animal Care and Use Committee and complied with National Institutes of Health and American Veterinary Medical Association guidelines.

Clinical data. All research samples were taken concurrently with clinical samples, which underwent review by an expert hematopathologist. Relevant clinical data was provided for each de-identified sample by the Johns Hopkins Kimmel Cancer Center Specimen Accessioning Core.

Statistical analysis. Means were compared between two groups using two-sided Student's t-test and between multiple groups using ANOVA. Categorical data was compared using the Fisher's exact test.

Example 1

ALDH activity distinguishes CD34$^+$CD38$^-$ leukemic cells from their normal counterparts. Normal bone marrow CD34$^+$CD38$^-$ cells consistently exhibited two, non-overlapping subpopulations by ALDH activity: one expressing low ALDH activity (CD34$^+$CD38$^-$ALDH$^{low}$) and another expressing high activity (CD34$^+$CD38$^-$ALDH$^{high}$) (FIG. 1A). The normal marrow CD34$^+$CD38$^-$ALDH$^{high}$ cells comprised an average of 10% (range 9-12%) of the total CD34$^+$ cells and 76% (range 61-85%) of the CD34$^+$CD38$^-$ cells. As few as 1000 of these CD34$^+$CD38$^-$ALDH$^{high}$ cells generated engraftment when transplanted into NSG mice (data not shown).

Initial AML analyses focused on patients with newly-diagnosed CBF leukemias, as the FISH-detectable abnormalities allowed quantification of the percentage of leukemic cells in isolated populations. In contrast to the normals, the CD34$^+$CD38$^-$ cells from all CBF AML patients exhibited three well-defined subpopulations by ALDH activity. In addition to the CD34$^+$CD38$^-$ALDH$^{low}$ and CD34$^+$CD38$^-$ALDH$^{high}$ populations, the CBF AML samples contained a population with intermediate ALDH activity (CD34$^+$CD38$^-$ALDH$^{int}$) that was not present in the normal donors (FIGS. 1B-C).

Figure 2:
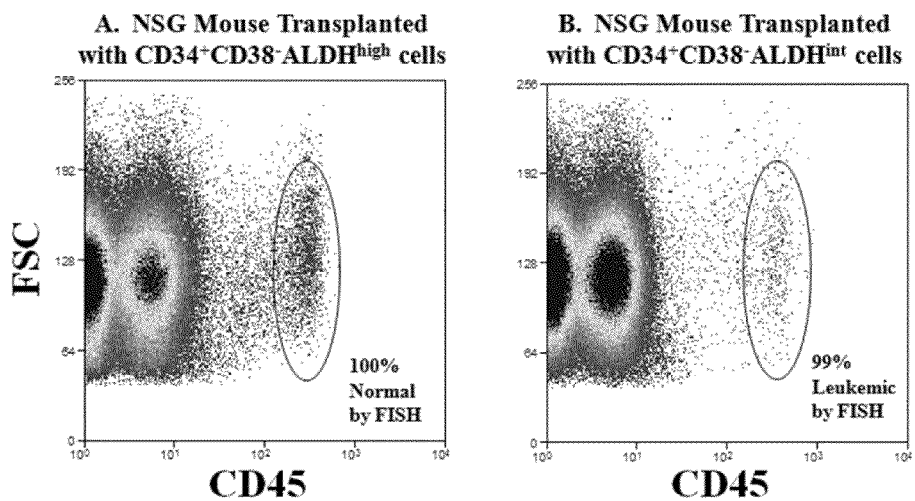
FIG. 2 depicts mouse engraftment. $CD34^+CD38^-ALDH^{high}$ or $CD34^+CD38^-ALDH^{int}$ cells were isolated from the diagnostic sample of a patient (#4) with Inv16 AML, and then transplanted into irradiated NSG mice. After 3 months, bone marrow was harvested from the transplanted mice; and engraftment was demonstrated by the presence of human $CD45^+$ cells (circled), which were then isolated and analyzed by FISH for the Inv16 abnormality. Representative plots of CD45 vs. forward scatter (FSC) are shown for mice transplanted with 1,000 cells of: (A) $CD34^+CD38^-ALDH^{high}$ cells that generated normal (by FISH) human hematopoietic engraftment of mice or (B) $CD34^+CD38^-ALDH^{int}$ cells that produced leukemic (by FISH) engraftment of mice. Human chimerism data are displayed in Table 3.

The CD34$^+$CD38$^-$ALDH$^{high}$ cells were rare in the newly-diagnosed CBF AML patients, constituting an average of only 0.12% (range 0.005-0.5%, p<0.001 vs. the normal samples) of the total CD34$^+$ cells and 1.24% (range 0.03-4.3%, p<0.001 vs. the normal samples) of the CD34$^+$CD38$^-$ cells. This CD34$^+$CD38$^-$ALDH$^{high}$ population was essentially devoid of cells with the leukemia-specific cytogenetic abnormality (Table 2). Similar to those isolated from normal donors, as few as 1000 of these cells yielded normal human engraftment of NSG mice (FIG. 2A; Table 3). Conversely, the CD34$^+$CD38$^-$ALDH$^{low}$ and the CD34$^+$CD38$^-$ALDH$^{int}$ populations from newly-diagnosed CBF AML patients were both virtually entirely leukemic by FISH (Table 2). As few as 1000 CD34$^+$CD38$^-$ALDH$^{int}$ cells produced leukemic engraftment of NSG mice (FIG. 2B; Table 3); no engraftment was seen with $10^3$-$10^5$ CD34$^+$CD38$^-$ALDH$^{low}$ cells. The CD34$^+$CD38$^-$ cells from other cytogenetic variants of AML, including those with normal cytogenetics, demonstrated similar staining patterns (FIG. 1D) and (where applicable) FISH results.

TABLE 2

Percentage of each sorted cell population positive for the leukemia-specific abnormality by FISH at diagnosis.

| Patient # | Total CD34$^+$ | CD34$^+$CD38$^-$ALDH$^{int}$ | CD34$^+$CD38$^-$ALDH$^{high}$ |
|---|---|---|---|
| Inv16* | | | |
| 1 | 96 | 96 | 2 |
| 2 | 96 | 98 | 4 |
| 3 | 81 | 92 | 3 |
| 4 | 62.5 | 88.2 | 1.8 |
| 5 | 99 | 98.5 | 0 |
| 6 | 99 | 99 | 0 |
| 22 | 87 | 98 | 1 |
| Average | 88.6 | 95.7 | 1.7 |
| Median | 96 | 98 | 1.8 |
| t(8; 21)$^\dagger$ | | | |
| 8 | 90 | 91 | 1.3 |
| 9 | 97 | 98 | 0 |
| 10 | 98 | 97 | 0 |
| 11 | 99 | 99 | 0 |
| Average | 96 | 96.3 | 0.3 |
| Median | 97.5 | 97.5 | 0 |
| Total Average | 91.3 | 95.9 | 1.2 |
| Total Median | 96 | 98 | 1 |

TABLE 3

| | Mouse Engraftment. | | | | | |
|---|---|---|---|---|---|---|
| | CD34$^+$ total | | CD34$^+$CD38$^-$ALDH$^{int}$ | | CD34$^+$CD38$^-$ALDH$^{high}$ | |
| Dose | Chimerism | FISH+ | Chimerism | FISH+ | Chimerism | FISH+ |
| 100,000 cells | 0.92% (±0.46%) | 95.5% | 1.21% (±0.49%) | 98.5% | ND | |
| 10,000 cells | 0.12% (±0.06%) | 98% | 0.19% (±0.06%) | 98.5% | 1.33% (±0.78%) | 4% |
| 1,000 cells | 0% | N/A | 0.14% (±0.12%) | 98% | 0.18% (±0.16%) | 0.5% |

Example 2

Presence of the CD34$^+$CD38$^-$ALDH$^{int}$ population following treatment predicts relapse. Of the 20 AML patients analyzed at diagnosis, three had primary refractory disease, one died during induction chemotherapy, one did not receive full induction or any consolidation chemotherapy due to medical complications, and two others had CD34⁻ leukemia. Of the 13 patients with CD34⁺ leukemia who achieved morphologic CR after induction chemotherapy, follow-up samples were available in nine. An additional seven AML patients who achieved CR, but in whom diagnostic samples were not available, were also followed: two starting after induction and five after consolidation therapy.

Figure 3:
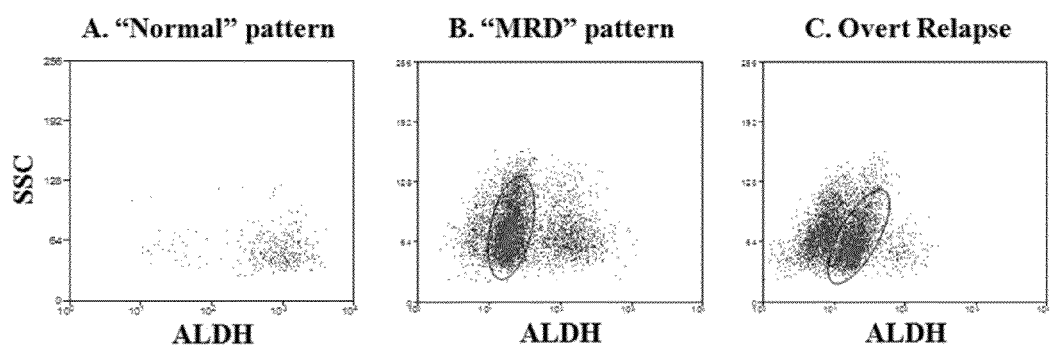
FIG. 3 shows staining patterns after therapy. Representative examples of (A) "normal" and (B) "MRD" staining patterns, as well as (C) overt clinical relapse. CD34+CD38− cells are displayed by ALDH vs. side scatter (SSC). (A) An AML patient (#17) with normal cytogenetics, in durable CR exhibiting the "normal" pattern with no detectable CD34+CD38− ALDH$^{int}$ population. The comparison diagnostic pattern for this patient is shown in FIG. 1D. (B) An AML patient (#1) with Inv16 AML, demonstrating the "MRD" pattern while still in CR; the circled CD34+CD38−ALDH$^{int}$ population was 95% leukemic by FISH. The comparison diagnostic pattern is depicted in FIG. 1C. (C) A patient (#9) with t(8; 21) AML, in overt relapse resembling the original diagnostic pattern (depicted in FIG. 1B). The percentage of CD34+CD38− cells comprised by the CD34+CD38−ALDH$^{int}$ and CD34+CD38− ALDH$^{high}$ populations are listed on each dot plot.
Figure 4:
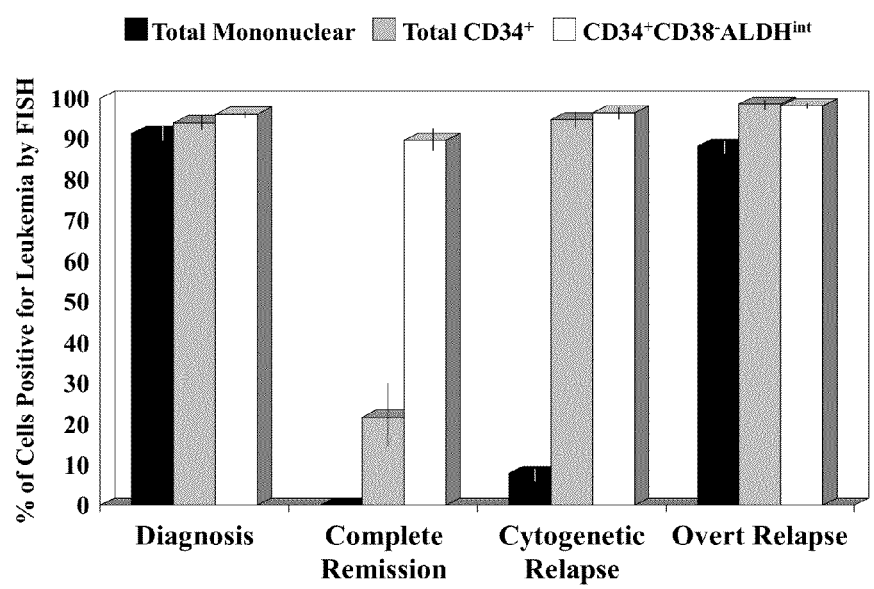
FIG. 4 depicts percentages of cell populations positive for leukemia by FISH in each disease phase. Data are displayed only for those patient samples with a FISH-detectable cytogenetic abnormality and a detectable CD34+CD38−ALDH$^{int}$ population. All three cell populations were highly leukemic at diagnosis. The CD34+CD38−ALDH$^{int}$ population was highly enriched for leukemic cells (≥85° A) in all disease phases, including complete cytogenetic remission (p>0.5). In contrast, the total CD34+ population contained only a minority of leukemic cells (average 22%, p<0.001 vs. diagnosis) in complete cytogenetic remission (patients #1, 15, & 16), but rose to ≥95% leukemic with progression to cytogenetic (patients #5, 7, & 12), or overt (patients #1 & 7-9) relapse (p=0.001 for differences in total CD34+ and in mononuclear cell FISH percentages across all four disease phases).

The CR samples exhibited two general patterns. Of the eight patients analyzed in first morphologic CR following recovery from induction and prior to consolidation chemotherapy, five patients (see table at FIG. 6) exhibited a "normal" pattern: a predominant $CD34^+CD38^-ALDH^{high}$ population and a smaller $CD34^+CD38^-ALDH^{low}$ population, with no discernable $CD34^+CD38^-ALDH^{int}$ population (FIG. 3A). Both CD34⁺CD38⁻ subpopulations in these remission patients were normal by FISH. The three patients who have consistently exhibited this "normal" pattern remain in CR, with an average follow-up of 293 (range 185-370) days since diagnosis. The other two patients ultimately relapsed; the $CD34^+CD38^-ALDH^{int}$ population was detected in both at the next follow-up interval, while still in CR after consolidation chemotherapy. The remaining three patients (FIG. 6) exhibited an "MRD" pattern upon recovery from induction, with a detectable $CD34^+CD38^-ALDH^{int}$ population, often without return of the $CD34^+CD38^-ALDH^{high}$ population to predominance (FIG. 3B). The $CD34^+CD38^-ALDH^{int}$ population was ≥85% leukemic by FISH in all three patients (FIG. 4). Two of these three patients relapsed within 33 days of detection of the "MRD" pattern and subsequently died (FIG. 6). The third patient underwent allogeneic transplantation in first CR because of adverse risk cytogenetics (complex karyotype, including deletion 7q) and has remained in CR for over 17 months.

Eleven AML patients who achieved morphologic CR with induction chemotherapy have been followed since completion of consolidation chemotherapy (FIG. 6). Of the seven patients with a consistently "normal" pattern after consolidation, none has yet relapsed, with an average duration of follow-up of 509 (range 185-810) days since diagnosis. However, all four of the patients with the "MRD" pattern post-consolidation have since relapsed (p=0.003 when compared to those patients with a consistently "normal" pattern), at an average of 53 (range 32-81) days after first detection of the "MRD" pattern (FIG. 6). Similar to the "MRD" cases after induction chemotherapy, the $CD34^+CD38^-ALDH^{int}$ population was overwhelmingly leukemic (≥95%) in those patients with FISH-detectable cytogenetic abnormalities (FIG. 4). One of the relapsed patients converted to a "normal" pattern after re-induction and allogeneic transplantation and has remained in second CR, for over one year. The "MRD" pattern persisted in two other patients, who achieved a second CR after re-induction; both of whom have subsequently relapsed again. Of note, the $CD34^+CD38^-ALDH^{int}$ population could not be detected in an additional two patients, who have been in CR for more than three years but have been followed only since their second year post-consolidation. Conversely, the $CD34^+CD38^-ALDH^{int}$ population was present in all six analyzed cases of overt clinical relapse (FIG. 3C).

Example 3

Figure 5:
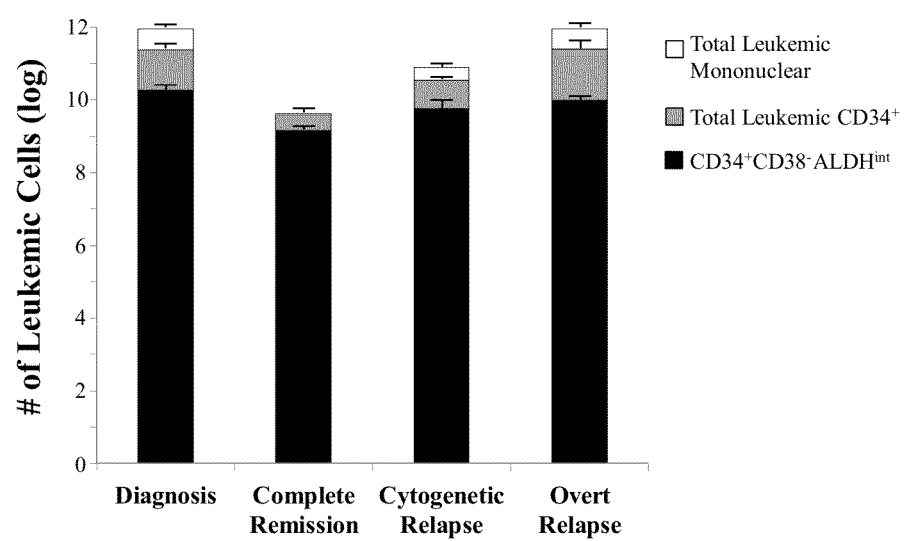
FIG. 5 shows the composition of the total leukemic burden by cell population in each disease phase. Data are displayed only for those patient samples with a FISH-detectable cytogenetic abnormality and a detectable CD34+CD38−ALDH$^{int}$ population. The total leukemic burden is assumed to be 1012 cells at diagnosis.37 Each vertical bar represents the total leukemic (mononuclear) cell burden (based on FISH) for each disease phase: initial diagnosis (patients #1-3, 5, 6, 8-13, & 22), cytogenetic complete remission (CR) with the "MRD" pattern (patients #1, 15, & 16), cytogenetic relapse (with FISH, but not morphologic evidence of disease; patients #5, 7, & 12), and at overt relapse (patients #1 & 7-9). The CD34+CD38−ALDHint cells represented an average of 2% (range 0.3-7%) of the total leukemic burden at initial diagnosis, 34% (range 9-51%) in cytogenetic CR, 8% (range 2-12%) in cytogenetic relapse, and 1% (range 0.5-2%) at overt relapse (p<0.001). The CD34+CD38−ALDH$^{int}$ population constituted an average of 8% (5-13%) of the total leukemic CD34+ cells at initial diagnosis, 34% (range 9-51%) in cytogenetic CR (p<0.001 vs. initial diagnosis), 18% (range 7-37%) in cytogenetic relapse, and 7% (range 2-16%) in overt relapse. Although the total leukemic burden decreased by over 2 logs from diagnosis to cytogenetic CR (p<0.001), the absolute size CD34+CD38−ALDH$^{int}$ population decreased only by 1 log (p=0.4).

MRD after chemotherapy is enriched for leukemic $CD34^+CD38^-ALDH^{int}$ cells. Although the three patients in cytogenetic CR exhibiting the "MRD" pattern had no morphologic, karyotypic, or FISH evidence of disease in the unfractionated marrow cells, the leukemia-specific abnormality was still detectable in a minority (average 22%, range 8-36%) of the total CD34⁺ cells and in the vast majority (average 90%, range 85-95%) of the $CD34^+CD38^-ALDH^{int}$ cells (FIG. 4). This leukemic $CD34^+CD38^-ALDH^{int}$ population, which represented only 0.15% (range 0.04-0.25%) of the total mononuclear cells, comprised an average of 34% (range 9-51%) of the total leukemic burden in these cytogenetic CR patients with the "MRD" pattern. In contrast, this population constituted only 2% (range 0.3-7%, p<0.001 vs. cytogenetic CR) of the total leukemic burden at diagnosis (FIG. 5). Moreover, although the total leukemic burden decreased by over 200-fold from diagnosis to cytogenetic CR (p<0.001), the $CD34^+CD38^-ALDH^{int}$ population decreased by only 13-fold (p=0.4) (FIG. 5).

In the three patients with cytogenetic, but no morphologic evidence of disease (i.e., cytogenetic relapse), an average of 8% (range 4.5-9.5%) of the unfractionated marrow cells were leukemic by FISH as compared to 96% (range 94-99%) of the $CD34^+CD38^-ALDH^{int}$ cells (p<0.001, FIG. 4). The relative size of the $CD34^+CD38^-ALDH^{int}$ fraction diminished in these early relapsing patients, representing an average of 8% (range 2-12%) of the total leukemic clone. At overt relapse, like at initial diagnosis, this population again comprised only a small fraction (average 1%, range 0.5-2%) of the total leukemic burden (FIG. 5).

This characteristic leukemic flow cytometric pattern was not seen in four of the 20 newly-diagnosed AML patients. In two AML patients, most of the leukemic CD34⁺CD38⁻ cells exhibited high ALDH activity, with no discernable separate population of normal $CD34^+CD38^-ALDH^{high}$ cells. One of these patients had normal cytogenetics with a FLT3 internal tandem duplication, and the other had complex cytogenetics that included deletions of chromosomes 5 and 7. Notably, both patients had primary refractory disease that ultimately proved fatal. In two additional patients, the diagnostic leukemic cytogenetic marker was present only in the CD34⁻ cells, as has been previously described in a minority of AML cases. One of these patients had an 11q23 abnormality and has since relapsed within a year of diagnosis; the other has remained in CR for more than one year since diagnosis and nine months since proceeding directly to allogeneic transplantation in first CR.

Using the methods of the present invention it was found that MRD was relatively enriched for the $CD34^+CD38^-ALDH^{int}$ cells. Although the total leukemic burden decreased by over 2 logs in patients with detectable MRD after a cytogenetic CR to induction therapy, the $CD34^+CD38^-ALDH^{int}$ cells decreased by only 1 log, implying that these cells were more drug-resistant than the bulk leukemic cells (FIG. 5). In addition, the $CD34^+CD38^-ALDH^{int}$ population was uniformly positive for the clonal leukemic cytogenetic marker (when assayable by FISH), was never present in normal donors, and produced leukemic engraftment when transplanted into immunodeficient mice. The percentage of these cells decreased as the leukemia recurred, consistent with dilution by their generated leukemic progeny (FIG. 5). Importantly, the presence of these cells during CR was highly predictive of subsequent AML relapse, supporting their clinical relevance. Indeed, six of the seven CR patients with the "MRD" pattern (i.e., a detectable $CD34^+CD38^-ALDH^{int}$ fraction) ultimately relapsed; the lone exception underwent allogeneic transplantation in first CR. Furthermore, the $CD34^+CD38^-ALDH^{int}$ population disappeared from those patients who achieved durable CR.

Interestingly, two of the primary refractory patients in this series had CD34⁺CD38⁻ leukemic cells with similar ALDH levels to normal HSCs. We recently found that CML LSCs also exhibit ALDH activity comparable to normal HSCs. ALDH expression decreases with HSC differentiation, and it is possible that the LSCs in most cases of AML arise from a less primitive progenitor, as has recently been suggested. Alternatively, those AML cases with CD34$^+$CD38$^-$ALDH-$^{high}$ leukemic cells may arise from more primitive cells, possibly translating to a poorer prognosis. While this remains to be proven, it has been reported that high ALDH activity in AML blasts does correlate with poorer outcomes.

Currently, cytogenetic and molecular aberrations are the best prognostic indicators for AML patients. However, these factors predict primarily for groups of patients and cannot prognosticate well for individual patients within any given risk strata. For example, CBF cytogenetic abnormalities are generally considered favorable; yet roughly half of these patients relapse. In contrast, the persistence of LSCs after therapy is a patient-specific variable and the methods of the present invention can serve as a powerful, individualized prognostic tool for patients. The detection of MRD appears to supply a lead time on the order of 1-3 months before overt clinical relapse, potentially affording sufficient time to prepare for allogeneic transplantation or enrollment on a clinical trial. The methods of the present invention provide a means to assess response at the level of the LSC and personalize care appropriately.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for identifying the presence of leukemic stem cells (LSC) in a sample from a subject suffering from acute myeloid leukemia (AML) comprising:
   a) obtaining a biological sample from a subject;
   b) isolating mononuclear cells from the sample of a);
   c) allowing the cells of b) to take up a fluorescent substrate for the enzyme aldehyde dehydrogenase (ALDH) and labeling the cells with a conjugated anti-CD34 monoclonal antibody and a conjugated anti-CD38 monoclonal antibody and a conjugated anti-CD38 monoclonal antibody;
   d) isolating CD34$^+$CD38$^-$ mononuclear cells or population of cells from the cells of c) using flow cytometry;
   e) measuring the ALDH activity of the cells or population of cells of d);
   f) providing a reference non-AML sample;
   g) comparing the levels of ALDH activity in the cells or population of cells from e) with the levels of ALDH activity in the cells or population of cells from the non-AML sample; and
   h) identifying the cells or population of cells from g) that have an intermediate level of ALDH activity (CD34$^+$CD38$^-$ALDH$^{int}$) in the sample from the subject when compared to the level of ALDH activity of the CD34$^+$CD38$^-$ in the non-AML sample as being LSC.

2. The method of claim 1, wherein the type of AML is core binding factor AML.

3. The method of claim 1, wherein the anti-CD34 monoclonal antibody is conjugated to phycoerythrin.

4. The method of claim 3, wherein the anti-CD38 monoclonal antibody is conjugated to allophycocyanin.

5. A method for prediction of an increased risk of relapse after treatment in a subject suffering from acute myeloid leukemia (AML) comprising:
   a) treating the subject diagnosed with AML with appropriate therapy;
   b) obtaining a post-therapy biological sample from a subject;
   c) allowing the cells of b) to take up a fluorescent substrate for the enzyme aldehyde dehydrogenase (ALDH) and labeling the cells with a conjugated anti-CD34 monoclonal antibody and a conjugated anti-CD38 monoclonal antibody and a conjugated anti-CD38 monoclonal antibody;
   d) isolating CD34$^+$CD38$^-$ mononuclear cells or population of cells from the cells of c) using flow cytometry;
   e) measuring the ALDH activity of the cells or population of cells of d);
   f) providing a reference non-AML sample;
   g) comparing the levels of ALDH activity in the cells or population of cells from e) with the levels of ALDH activity in the cells or population of cells from the non-AML sample; and
   h) identifying the cells or population of cells from g) that have an intermediate level of ALDH activity (CD34$^+$CD38$^-$ALDH$^{int}$) in the sample from the subject when compared to the level of ALDH activity of the CD34$^+$CD38$^-$ in the non-AML sample as being LSC,
   i) identifying the cells or population of cells from g) that have an intermediate level of ALDH activity (CD34$^+$CD38$^-$ALDH$^{int}$) in the sample from the subject when compared to the level of ALDH activity of the CD34$^+$CD38$^-$ in the non-AML sample as being LSC; and j) determining that the subject has an increased risk for relapse of AML, and identifying that subject for further treatment, when the presence of LSC are detected in the sample from the subject.

6. The method of claim 5, wherein the type of AML is core binding factor AML.

7. The method of claim 5, wherein the anti-CD34 monoclonal antibody is conjugated to phycoerythrin.

8. The method of claim 7, wherein the anti-CD38 monoclonal antibody is conjugated to allophycocyanin.

9. A method for treatment of a subject suffering from acute myeloid leukemia (AML) comprising:
   a) obtaining biological sample from a subject;
   b) isolating mononuclear cells from the sample of a);
   c) allowing the cells of b) to take up a fluorescent substrate for the enzyme aldehyde dehydrogenase (ALDH) and labeling the cells with a conjugated anti-CD34 monoclonal antibody and a conjugated anti-CD38 monoclonal antibody and a conjugated anti-CD38 monoclonal antibody;
   d) isolating $CD34^+CD38^-$ mononuclear cells or population of cells from the cells of c) using flow cytometry;
   e) measuring the ALDH activity of the cells or population of cells of d);
   f) providing a reference non-AML sample;
   g) comparing the levels of ALDH activity in the cells or population of cells from e) with the levels of ALDH activity in the cells or population of cells from the non-AML sample; and
   h) identifying the cells or population of cells from g) that have an intermediate level of ALDH activity ($CD34^+CD38^-ALDH^{int}$) in the sample from the subject when compared to the level of ALDH activity of the $CD34^+CD38^-$ in the non-AML sample as being LSC;
   i) treating the subject suffering from AML with appropriate therapy when LSC are identified in the sample from the subject;
   j) repeating steps a) to h); and
   k) determining that the subject has completed treatment for AML when the presence of LSC are not detected.

10. The method of claim 9, wherein the method further comprises repeating steps a) to i) if the presence of LSC are detected.

11. The method of claim 9, wherein the type of AML is core binding factor AML.

12. The method of claim 9, wherein the anti-CD34 monoclonal antibody is conjugated to phycoerythrin.

13. The method of claim 12, wherein the anti-CD38 monoclonal antibody is conjugated to allophycocyanin.

* * * * *

UNITED STATES PATENT AND TRADEMARK OFFICE
CERTIFICATE OF CORRECTION

PATENT NO. : 9,012,215 B2  
APPLICATION NO. : 13/625369  
DATED : April 21, 2015  
INVENTOR(S) : Gerber et al.

Page 1 of 1

It is certified that error appears in the above-identified patent and that said Letters Patent is hereby corrected as shown below:

In the Specification

Column 1, Line 14, replace the second paragraph as follows:  
STATEMENT OF GOVERNMENTAL INTEREST  
This invention was made with government support under CA015396, CA070970, CA070095, and HL007585, awarded by the National Institutes of Health. The government has certain rights in the invention.

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*